United States Patent
Byron et al.

(10) Patent No.: US 8,785,466 B2
(45) Date of Patent: Jul. 22, 2014

(54) METHODS OF USING PROTEINACIOUS CHANNELS TO IDENTIFY PHARMACEUTICAL TREATMENTS AND RISKS, AND TREATMENTS RESULTING THEREFROM

(75) Inventors: Kenneth L. Byron, Chicago, IL (US); Lioubov I. Brueggemann, Lombard, IL (US)

(73) Assignee: Loyola University Chicago, Maywood, IL (US)

( * ) Notice: Subject to any disclaimer, the term of this patent is extended or adjusted under 35 U.S.C. 154(b) by 408 days.

(21) Appl. No.: 12/609,724

(22) Filed: Oct. 30, 2009

(65) Prior Publication Data
US 2010/0113553 A1 May 6, 2010

Related U.S. Application Data

(60) Provisional application No. 61/110,152, filed on Oct. 31, 2008.

(51) Int. Cl.
| | | |
|---|---|---|
| *A61K 31/505* | (2006.01) | |
| *A61K 31/44* | (2006.01) | |
| *A61K 31/41* | (2006.01) | |
| *A61K 31/415* | (2006.01) | |
| *A61K 31/155* | (2006.01) | |
| *A61K 31/439* | (2006.01) | |
| *A61K 31/135* | (2006.01) | |
| *A61K 31/137* | (2006.01) | |
| *A61K 31/436* | (2006.01) | |

(52) U.S. Cl.
CPC .............. *A61K 31/155* (2013.01); *A61K 31/439* (2013.01); *A61K 31/135* (2013.01); *A61K 31/137* (2013.01); *A61K 31/436* (2013.01)
USPC ........... 514/273; 514/275; 514/353; 514/364; 514/406

(58) Field of Classification Search
CPC ... A61K 45/06; A61K 31/155; A61K 31/135; A61K 31/137; A61K 31/436; A61K 31/439
USPC ......................... 514/273, 275, 353, 364, 406
See application file for complete search history.

(56) References Cited

U.S. PATENT DOCUMENTS

| | | | |
|---|---|---|---|
| 5,466,823 A | 11/1995 | Talley et al. | |
| 5,563,165 A | 10/1996 | Talley et al. | |
| 5,760,068 A | 6/1998 | Talley et al. | |
| 5,972,986 A | 10/1999 | Seibert et al. | |

FOREIGN PATENT DOCUMENTS

WO WO2007/087424 * 2/2007

OTHER PUBLICATIONS

Ohya et al., Cir. Res. 2003;92:1016-1023.*
Patrick Delmas and David A. Brown; Pathways Modulating Neural KNCQ/M (Kv7) Potassium Channels; University College London.
Jon Robbins; KCNQ potassium channels: physiology, pathophysiology, and pharmacology; Centre for Neuroscience Research; London; 2001.
Patricia McGettigan; David Henry; Cardiovascular Risk and Inhibition of Cyclooxygenase: A Systematic Review of the Observational Studies of Selective and Nonselective Inhibitors of Cyclooxygenase 2; JAMA; 2006; 296 (13): 1633-1644.
William B. White, Christine R. West, Jeffrey Borer, Philip Gorelick, Lisa Lavange, Sharon Pan, Ethan Weiner, and Kenneth Verburg; Risk of Cardiovascular Events in Patients Receiving Celecoxib: A Meta-Analysis of Randomized Clinical Trials; 2007 Elsevier Inc.
Lioubov I. Brueggemann, Alexander R. Mackie, Bharath K. Mani, Leanne L. Cribbs and Kenneth L. Byron; Differential Effects of Selective COX-2 Inhibitors on Vascular Smooth Muscle Ion Channels May Account for Differences in Cardiovascular Risk Profiles, 2009.
Alexander R. Mackie and Kenneth L. Byron; Cardiovascular KCNQ (Kv7) Potassium Channels: Physiological Regulators and New Targets for Therapeutic Intervention; Molecular Pharmacology; vol. 74, No. 5; 2008.
Jiuxiang Zhu, Xueqin Song, Ho-Pi Lin, Donn C. Young, Shunqi Yan, Victor E. Marquez, Ching-Shih Chen; Using Cyclooxygenase-2 Inhibitors as Molecular Platforms to Develop a New Class of Apoptosis-Inducing Agents; Journal of the National Cancer Institute; vol. 94, No. 23, Dec. 4, 2002.
Axel H. Schonthal; Antitumor properties of dimenthyl-celecoxib, a derivative of celecoxib that does not inhibit cyclooxygenase-2: implications for glioma therapy; Department of Molecular Microbiology and Immunology, Keck School of Medicine; Neurosurg Focus 20; 2006.

(Continued)

*Primary Examiner* — Sam-Ming Hui
(74) *Attorney, Agent, or Firm* — Hartman Global IP Law; Gary M. Hartman; Domenica N. S. Hartman

(57) ABSTRACT

Methods and therapeutic strategies utilizing proteinacious channels in lipid membranes of mammalian cells. The methods entail administering a pharmaceutical to a lipid membrane of a mammalian cell, and then determining the effect of the pharmaceutical on the electrophysiology of at least one vascular proteinacious channel of the lipid membrane, wherein the vascular proteinacious channel is a vascular Kv7 potassium channel and/or a vascular L-type calcium channel. The method can be used to identify pharmaceuticals that may be used to treat hypertension and/or vasospastic conditions, or to perform drug screening to assess potential cardiovascular risk of pharmaceuticals.

15 Claims, No Drawings

(56) References Cited

OTHER PUBLICATIONS

Lioubov I. Brueggemann, Christopher J. Moran, John A. Barakat, Jay Z. Yeh, Leanne L. Cribbs, and Kenneth L. Byron; Vasopressin stimulates action potential firing by protein kinase C-dependent inhibition of KCNQ5 in A7r5 rat aortic smooth muscle cells; American Journal Physiological Heart Circ Physiol 292; H1352-H1363; 2007.

S.M.L. Abrams, L.R.I. Baker, P. Crome, A.S.T. White, A. Johnston, S.I. Ankier, S.J. Warrington, P. Turner and G. Niebch; Pharmacokinetics of flupirtine in elderly volunteers and in patients with moderate renal impairment; Postgraduate Medical Journal (1988) 64, 361-363.

W.M. Herrmann, U. Kern and M. Aigner; On the adverse reactions and efficacy of long-term treatment with flupirtine: preliminary results of an ongoing twelve-month study with 200 patients suffering from chronic pain states in arthrosis or arthritis; Postgraduate Medical Journal (1987) 63, 87-103.

Alexander R. Mackie, Lioubov I. Brueggemann, Kyle K. Henderson, Aaron J. Shiels, Leanne L. Cribbs, Karie E. Scrogin, and Kenneth L. Byron; Vascular KCNQ Potassium Channels as Novel Targets for the Control of Mesenteric Artery Constriction by Vasopressin, Based on Studies in Single Cells, Pressurized Arteries, and in Vivo Measurements of Mesenteric Vascular Resistance; The Journal of Pharmacology and Experimental Therapeutics; JPET 325: 475-483, 2008.

Axel H. Schonthal, Thomas C. Chen, Florence M. Hofman, Stan G. Louis and Nicos A. Petasis; Celecoxib analogs that lack COX-2 inhibitory function: preclinical development of novel anticancer drugs; Informa Healthcare; 1354-3784; 2008.

* cited by examiner

METHODS OF USING PROTEINACIOUS CHANNELS TO IDENTIFY PHARMACEUTICAL TREATMENTS AND RISKS, AND TREATMENTS RESULTING THEREFROM

CROSS REFERENCE TO RELATED APPLICATIONS

This application claims the benefit of U.S. Provisional Application No. 61/110,152, filed Oct. 31, 2008, the contents of which are incorporated herein by reference.

BACKGROUND OF THE INVENTION

The present invention generally relates to therapeutic strategies utilizing proteinacious channels in lipid membranes of mammalian cells. More particularly, this invention relates to the utilization of the electrophysiology of vascular Kv7 potassium channels and/or vascular L-type calcium channels, for example, to identify new pharmaceuticals that may be used to treat cardiovascular conditions, and to perform drug screening to assess potential cardiovascular risk of pharmaceuticals.

Mammalian cells, including the vascular smooth muscle cells (VSMCs) of artery vessel walls, are surrounded by a lipid membrane which functions as a barrier to diffusion of many soluble substances, including ions, into and out of the cells. Proteinacious channels integrated into these lipid membranes allow ions to cross the lipid membrane when the channels are open. A portion of these proteinacious channels is selective for potassium ions ($K^+$), and will be referred to as potassium channels or $K^+$ channels. Still other proteinacious channels are selective for calcium ions ($Ca^{2+}$), and will be referred to as calcium channels or $Ca^{2+}$ channels. Under normal circumstances, potassium ions ($K^+$) are typically present inside the cell at concentrations about twenty-five times higher as compared to their corresponding concentration outside the cell. When these potassium channels open (activate), potassium ions ($K^+$) tend to leak out of the cell through these potassium channels, resulting in a measurable electrical current across the membrane. This electrical current establishes an electrical charge difference across the lipid membrane (membrane voltage), resulting in the polarization of the membrane. Polarization of the membranes of vascular smooth muscle cells has a profound effect on the function of voltage-sensitive L-type $Ca^{2+}$ channels in these cells and is a primary determinant of the extent to which arteries constrict or dilate. KCNQ voltage-activated $K^+$ channels (also known as the Kv7 family) play an important role in regulating the membrane voltage of many excitable tissues. See, for example, Delmas et al., "Pathways modulating neural KCNQ/M (Kv7) potassium channels," Nat Rev Neurosci 6(11):850-862 (2005); and Robbins et al., KCNQ potassium channels: physiology, pathophysiology, and pharmacology," Pharmacol Ther 90(1):1-19 (2001). Recently, KCNQ5 (Kv7.5) channels were determined to be expressed and functional in vascular smooth muscle cells.

Cyclooxygenase-2 (COX-2) inhibitors are important members of the family of non-steroidal anti-inflammatory drugs (NSAIDs). Celebrex® (celecoxib) and Vioxx® (rofecoxib) were introduced in 1999 and rapidly became frequently prescribed for clinical use as analgesic/anti-inflammatory agents because they prevent the generation of prostaglandins involved in inflammation and pain, while sparing the beneficial effects of cyclooxygenase-1 (COX-1)-generated prostanoids. However, COX-2 inhibitors have been under intense scrutiny since 2004 when Vioxx® was voluntarily withdrawn from the market because of a reported increased risk of myocardial infarction and stroke in patients taking the drug for prolonged periods of time.

A systematic review of randomized clinical trials of COX inhibitors revealed that rofecoxib, a highly COX-2-selective agent, and diclofenac, an NSAID with COX-2/COX-1 selectivity similar to celecoxib, both significantly increased the risk of cardiovascular (CV) events. In contrast, a number of clinical studies failed to demonstrate an increased CV risk with celecoxib relative to placebo. See, for example, McGettigan et al., "Cardiovascular Risk and Inhibition of Cyclooxygenase: A Systematic Review of the Observational Studies of Selective and Nonselective Inhibitors of Cyclooxygenase 2," Journal of the American Medical Association 296:1633-1644 (2006), and White et al., "Risk of Cardiovascular Events in Patients Receiving Celecoxib: A Meta-Analysis of Randomized Clinical Trials," The American Journal of Cardiology 99(1):91-98 (2007). The reasons for the differences between celecoxib and other COX-2 inhibitors have been widely debated.

HERG (human ether-a-go-go related gene) encodes a particular type of potassium channel (Kv11.1) that contributes to the electrical activity of the heart. To avoid unwanted cardiac side effects, new drugs in development are commonly screened for effects on Kv11.1 potassium channel currents using cultured cells engineered to express large numbers of these channels. In contrast, vascular Kv7 channels have not been recognized as a potential site of adverse (or beneficial) drug action and therefore no vascular Kv7 channel screening assays have been developed. Prior to a recent report (Brueggemann et al., "Differential Effects of Selective COX-2 Inhibitors on Vascular Smooth Muscle Ion Channels May Account for Differences in Cardiovascular Risk Profiles," Molecular Pharmacology 76: 1053-1061 (2009)), COX inhibitors had not been reported to exert any effects on vascular smooth muscle Kv7 channels or vascular smooth muscle L-type $Ca^{2+}$ channels, and therefore no therapeutic strategies have been proposed to use these drugs to treat vasospastic conditions that can lead to heart attacks or strokes.

HERG channel screening assays do not detect effects of drugs on vascular Kv7 channel activity and therefore are not useful for predicting potential adverse cardiovascular side effects associated with such activity or for predicting potential beneficial therapeutic effects associated with such activity.

BRIEF DESCRIPTION OF THE INVENTION

The present invention provides methods and therapeutic strategies utilizing the electrophysiology of proteinacious channels in lipid membranes of mammalian cells to identify pharmaceutical treatments and risks, and to treatments arising from such methods.

According to a first aspect of the invention, a method is provided that entails administering a pharmaceutical to a lipid membrane of a mammalian cell, and then determining the effect of the pharmaceutical on the electrophysiology of at least one vascular proteinacious channel of the lipid membrane, wherein the vascular proteinacious channel is a vascular Kv7 potassium channel and/or a vascular voltage-sensitive L-type calcium channel.

According to another aspect of the invention, the method can be used to identify pharmaceuticals that may be used to treat, for example, vasospastic conditions. Yet another aspect of the invention is to employ the method to perform drug screening to assess potential cardiovascular risk of pharmaceuticals.

Other aspects and advantages of this invention will be better appreciated from the following detailed description.

DETAILED DESCRIPTION OF THE INVENTION

The present invention arises from investigations that suggest that differential effects of Vioxx® (rofecoxib), Celebrex® (celecoxib), and other COX-2 inhibitors on vascular Kv7 channels and L-type $Ca^{2+}$ channels may account for the differences in cardiovascular risk profiles of these drugs. In particular, investigations leading to the present invention have identified celecoxib as an effective activator of vascular Kv7 channels and an effective inhibitor of vascular L-type $Ca^{2+}$ channels, whereas rofecoxib does not exhibit either effect. These investigations are reported in Brueggemann et al., "Differential Effects of Selective COX-2 Inhibitors on Vascular Smooth Muscle Ion Channels May Account for Differences in Cardiovascular Risk Profiles," Molecular Pharmacology 76: 1053-1061 (2009), whose entire contents are incorporated herein by reference. According to particular aspects of the invention, such differential effects provide a basis for using vascular Kv7 potassium channel electrophysiology, for example, to identify new pharmaceuticals that may be capable of treating vasospastic conditions, and to perform drug screening to assess potential cardiovascular risk of pharmaceuticals.

In studies leading to the present invention and reported in Mackie et al., "Cardiovascular KCNQ (Kv7) Potassium Channels: Physiological Regulators and New Targets for Therapeutic Intervention," Mol Pharmacol 74:1171-1179 (2008) (incorporated herein by reference), Kv7 channel modulators used clinically to treat a number of neuronal disorders were determined to have pronounced effects on vascular Kv7 channels. The studies further showed that these effects were associated with corresponding changes in vascular tone in isolated pressurized rat mesenteric arteries and changes in systemic blood pressure and mesenteric vascular resistance in live rats. In subsequent studies reported in Brueggemann et al. (supra), by screening drugs with structures similar to Kv7 channel modulators but used for other clinical applications, the present invention has identified the COX-2 inhibitor celecoxib (as disclosed in, for example, U.S. Pat. Nos. 5,466,823, 5,563,165, 5,760,068 and 5,972,986, whose contents regarding the chemical structure of celecoxib are incorporated herein by reference) as a potent and effective activator of vascular Kv7 channels. This conclusion is believed to have important and broader implications relating to the treatment of vasospastic conditions with pharmaceuticals, and screening to assess potential cardiovascular risk of pharmaceuticals.

Preliminary findings leading to this invention were derived from electrophysiological analyses of the effects of celecoxib and rofecoxib on rat and human vascular smooth muscle cell (VSMC) ion channels. The activities were measured for two types of ion channels that are perhaps the most important in determining the contractile state of vascular smooth muscle cells: potassium ($K^+$) channels, which determine the resting membrane voltage, and voltage-sensitive calcium ($Ca^{2+}$) channels (VSCC), the activation of which allows $Ca^{2+}$ influx and vasoconstriction. These investigations showed that both types of ion channels are affected by celecoxib, and that celecoxib is a potent activator of Kv7.5 potassium channels and an inhibitor of L-type $Ca^{2+}$ channels in vascular smooth muscle cells. These effects, which were apparent at concentrations of celecoxib often achieved with clinical therapy, had never been reported previously and may account for the reduced risk of cardiovascular side effects with celecoxib treatment as compared to rofecoxib. Rofecoxib did not mimic celecoxib in its effects on either Kv7.5 channels or L-type VSCC. The actions of these drugs can be assessed at the level of isolated arterial myocytes and intact pressurized arteries. Also demonstrated was the ability to monitor effects of Kv7 channel activators on systemic blood pressure and mesenteric vascular resistance in live rats. These functional assays provide a means for screening new drugs as well as drugs already in clinical use, and a means for predicting potential CV side effects.

The significance of the above extends beyond the well known and abundant use of COX-2 inhibitors as anti-inflammatory agents. In recent years there has been an explosion of interest in the use of COX-2 inhibitors as anti-cancer drugs. In cancers and abnormal growths in the intestinal tract, COX inhibitors have been shown to reduce the occurrence of cancers and pre-cancerous growths. As reported by Zhu et al. in "Using Cyclooxygenase-2 Inhibitors as Molecular Platforms to Develop a New Class of Apoptosis-Inducing Agents," J Natl Cancer Inst 94(23):1745-1757 (2002), whose contents are incorporated herein by reference, several dozen analogs of celecoxib have been generated with small alterations in their chemical structures. Consistent with the ordinary meaning of the word "analog" in the pharmaceutical industry, whose research activities commonly involve creating and testing analogs of compounds as part of structure-activity relationship studies, an "analog" of celecoxib refers to a compound having a structure similar to that of celecoxib, but differing by having different chemical substitutions around its core structure (the diarylpyrazole moiety). Some of the analogs reported by Zhu et al. retained COX-2 inhibitory activity, whereas many others did not. As reported by Zhu et al. as well as Schonthal et al. in "Celecoxib analogs that lack COX-2 inhibitory function: preclinical development of novel anticancer drugs," Expert Opinion on Investigational Drugs 17(2):197-208 (2008), the anti-tumor potency of celecoxib analogs do not correlate with COX-2 inhibitory activity, suggesting that inhibition of COX-2 is not essential for the anti-cancer effects. One of these compounds, 2,5-dimethyl-celecoxib, which has no detectable COX-2 inhibitory activity, has been reported to display stronger anti-cancer activity than celecoxib itself. Schönthal "Antitumor properties of dimethyl-celecoxib, a derivative of celecoxib that does not inhibit cyclooxygenase-2: implications for glioma therapy," Neurosurg Focus 20(4):E21 (2006). In studies leading to the present invention, 2,5-dimethyl-celecoxib was determined to be a potent activator of vascular Kv7 channels and an inhibitor of vascular L-type calcium channels. The mechanisms underlying the anti-cancer efficacy of celecoxib and its analogs are the subject of much controversy. The anti-cancer efficacy of celecoxib analogs may relate to their previously unrecognized effects on vascular smooth muscle Kv7 channels or other vascular ion channels. Characterization of these effects may also help to predict potential cardiovascular side effects of celecoxib or its analogs when used as anti-cancer agents or to develop new clinical applications for celecoxib or its analogs (for example, 2,5-dimethyl-celecoxib) as, for example, an antivasospastic and/or antihypertensive agent.

An additional preferred aspect of the invention is to develop new therapeutic applications for Kv7 channel modulators based on the roles of these channels in vascular smooth muscle physiology. In studies leading to the present invention, the signal transduction process by which vasoactive hormones induce constriction of arteries was determined to involve inhibition of Kv7.5 K⁺ channels. Mackie et al. (above) and Brueggemann et al., "Vasopressin stimulates action potential firing by protein kinase C-dependent inhibition of KCNQ5 in A7r5 rat aortic smooth muscle cells," Am J Physiol Heart Circ Physiol 292(3):H1352-H1363 (2007), disclose what is believed to be the first evidence that these channels are regulated by the vasoconstrictor hormone, arginine-vasopressin (AVP), acting on vascular smooth muscle cells, and that this effect is central to its physiological vasoconstrictor actions. The vasoconstrictor actions of AVP are important in terms of normal physiological blood pressure regulation, and AVP has also been implicated in a number of cardiovascular diseases, including spasm of the cerebral vasculature that occurs in a condition called subarachnoid hemorrhage (SAH). Cerebral vasospasm represents a significant clinical problem and is a major cause of stroke in the United States. The mechanisms underlying vasospasm after SAH are an area of active investigation in which no consensus has been reached. Furthermore, clinical therapies to prevent vasospasm or reduce its detrimental effects are currently inadequate. The present invention proposes that Kv7 channel activators, including celecoxib, may be used as a novel therapy to protect against SAH-induced stroke.

The scope of the present invention further encompasses the tools used to measure vascular Kv7 channel activities and/or functional contributions of these channels in vascular smooth muscle cells. To screen new or existing drugs for potential vascular side effects associated with changes in vascular smooth muscle Kv7 channel activity, varying concentrations of the drugs should be applied to cells expressing these channels while recording the electrical activity that results from changes in channel opening. Patch clamp electrophysiological techniques are typically used for such recordings, and investigations leading to the present invention have developed patch clamp recording techniques for accurate and sensitive monitoring of Kv7 channel activity in vascular smooth muscle cells. Drugs that significantly increase vascular smooth muscle Kv7 channel activity at concentrations achieved clinically are expected to have reduced risk of cardiovascular side effects, whereas drugs that reduce vascular smooth muscle Kv7 channel activity may have increased risk of cardiovascular side effects. For example, flupirtine is a known Kv7 channel activator used to treat pain; plasma concentrations achieved clinically can be as high as about 12 µM with a 100 mg dose (Abrams et al., "Pharmacokinetics of flupirtine in elderly volunteers and in patients with moderate renal impairment," Postgraduate Medical Journal, 64: 361-363 (1988)) and doses up to about 600 mg are routinely given to treat chronic pain. In patients with rheumatic disease, flupirtine (about 100 to 600 mg per day) was reported to lower systolic blood pressure (Herrmann et al., "On the adverse reactions and efficacy of long-term treatment with flupirtine: preliminary results of an ongoing twelve-month study with 200 patients suffering from chronic pain states in arthrosis or arthritis," Postgraduate Medical Journal, 63: 87-103 (1987)). This might have been predicted based on observations made during investigations leading to the present invention that a concentration of 10 µM flupirtine was sufficient to increase vascular Kv7 current by 100%. Further indications to support such predictions may be obtained by measuring the effects of drugs on constriction/dilation of pressurized arteries. Flupirtine (about 10 to 40 µM) was found to dilate rat mesenteric arteries (Mackie et al., "Vascular KCNQ potassium channels as novel targets for the control of mesenteric artery constriction by vasopressin, based on studies in single cells, pressurized arteries, and in vivo measurements of mesenteric vascular resistance," Journal of Pharmacology and Experimental Therapeutics 325: 475-483 (2008)).

According to an aspect of the invention, screening of drugs for effects on vascular Kv7 channel activity may identify new drugs or new applications for existing drugs for the treatment of cardiovascular diseases. For example, by screening COX inhibitors for effects on vascular Kv7 channels, the present invention identified celecoxib as a potent vascular Kv7 channel activator and determined that celecoxib is a potent vasodilator that can reverse AVP-induced basilar artery constriction. On this basis, the present invention proposes a treatment in which celecoxib is used effectively to reduce stroke associated with spasm of basilar and/or cerebral arteries.

Prior to investigations leading to the invention, drugs in clinical use had not been screened for effects on vascular Kv7 channels. Such screening might have predicted the differential effects of celecoxib and rofecoxib in terms of their potential risks of adverse cardiovascular events. Furthermore, had such screening methods been employed previously, celecoxib might have been previously identified as a potentially useful anti-vasospastic agent. Therefore, by employing screening techniques to evaluate the effects of new or existing drugs on vascular Kv7 channels, adverse side effects may be prevented and new therapeutic applications for drugs may be realized.

The present invention is believed to provide a basis for the effect of COX-2 inhibitors on vascular Kv7 channels and for performing drug screening using Kv7 channel electrophysiology to assess potential cardiovascular risk. Furthermore, the determination that celecoxib and its analog 2,5-dimethyl-celecoxib are effective activators of vascular Kv7 channels and effective inhibitors of vascular L-type $Ca^{2+}$ channels is also believed to have been unknown prior to the present invention. As such, the present invention also encompasses methods of treating a hypertensive or vasospastic condition in a living body by administering a pharmaceutical, for example, celecoxib or 2,5-dimethyl-celecoxib, as an antivasospastic and/or antihypertensive agent that can be administered in a therapeutic amount sufficient to activate vascular Kv7 potassium channels and/or inhibit vascular L-type calcium channels.

While the invention has been described in terms of specific embodiments, it is apparent that the underlying discoveries and teachings presented herein could be adopted by those skilled in the art for uses beyond those suggested herein. Therefore, the scope of the invention is to be limited only by the following claims.

The invention claimed is:

1. A method utilizing proteinacious channels in a lipid membrane of a mammalian cell, the method comprising:
   administering a pharmaceutical to a lipid membrane of a mammalian cell;
   measuring an electrical activity across the lipid membrane to determine an effect of the pharmaceutical on the electrophysiology of arterial Kv7 potassium channels of the lipid membrane; and then
   identifying pharmaceutical treatments for hypertensive, cancer, vasospastic, or cardiovascular medical conditions or risks of the pharmaceutical based on the electrical activity caused by the pharmaceutical,
   wherein the medical conditions are affected by the electrophysiology of arterial Kv7 potassium channels; and
   wherein pharmaceutical treatments for hypertensive, cancer, vasospastic, or cardiovascular medical conditions are identified if the effect of the pharmaceutical is to activate the arterial Kv7 potassium channels during the step of measuring the electrical activity, and risks of the pharmaceutical are identified if the effect of the pharmaceutical is to inhibit the arterial Kv7 potassium channels during the step of measuring the electrical activity.

2. The method according to claim 1, wherein the step of measuring the electrical activity determines the effect of the pharmaceutical on currents generated by the arterial Kv7 potassium channels.

3. The method according to claim 1, further comprising administering the pharmaceutical to a living body if the effect of the pharmaceutical is to activate the arterial Kv7 potassium channels during the step of measuring the electrical activity.

4. The method according to claim 1, wherein the step of administering a pharmaceutical comprises administering the pharmaceutical to cultured cells engineered to express arterial Kv7 potassium channels.

5. The method according to claim 1, wherein the mammalian cell is an arterial smooth muscle cell.

6. The method according to claim 1, wherein the step of identifying pharmaceutical treatments for medical conditions or risks of the pharmaceutical is performed to identify pharmaceuticals for treating cardiovascular conditions if the effect of the pharmaceutical is to activate the arterial Kv7 potassium channels during the step of measuring the electrical activity.

7. The method according to claim 1, further comprising administering the pharmaceutical to a living body to treat a hypertensive or vasospastic condition if the effect of the pharmaceutical is to activate the arterial Kv7 potassium channels.

8. The method according to claim 6, further comprising administering the pharmaceutical to a living body that has suffered a subarachnoid hemorrhage if the effect of the pharmaceutical is to activate the arterial Kv7 potassium channels during the step of measuring the electrical activity.

9. The method according to claim 1, wherein the method is a drug screening procedure to assess potential cardiovascular risks of the pharmaceutical.

10. The method according to claim 9, wherein the step of measuring the electrical activity determines the effect of the pharmaceutical on currents generated by the arterial Kv7 potassium channels.

11. The method according to claim 9, further comprising administering the pharmaceutical to a living body if the effect of the pharmaceutical is to activate or inhibit the arterial Kv7 potassium channels during the step of measuring the electrical activity.

12. The method according to claim 9, further comprising administering the pharmaceutical to a living body to treat cancer if the effect of the pharmaceutical is to activate the arterial Kv7 potassium channels during the step of measuring the electrical activity.

13. A method utilizing proteinacious channels in a lipid membrane of a mammalian cell, the method comprising:
   administering a pharmaceutical to a lipid membrane of a mammalian cell; and then
   determining an effect of the pharmaceutical on the electrophysiology of vascular Kv7 potassium channels of the lipid membrane;
   wherein the pharmaceutical is a COX-2 inhibitor.

14. The method according to claim 1, wherein the pharmaceutical is not a COX-2 inhibitor.

15. The method according to claim 13, wherein the pharmaceutical is celecoxib or 2,5-dimethyl-celecoxib.

* * * * *